(12) United States Patent
Betts

(10) Patent No.: US 8,075,556 B2
(45) Date of Patent: Dec. 13, 2011

(54) HIGH FREQUENCY EPIDURAL NEUROMODULATION CATHETER FOR EFFECTUATING RF TREATMENT IN SPINAL CANAL AND METHOD OF USING SAME

(76) Inventor: Andres Betts, San Clemente, CA (US)

( * ) Notice: Subject to any disclaimer, the term of this patent is extended or adjusted under 35 U.S.C. 154(b) by 1239 days.

(21) Appl. No.: 11/752,210

(22) Filed: May 22, 2007

(65) Prior Publication Data

US 2007/0276319 A1    Nov. 29, 2007

Related U.S. Application Data

(60) Provisional application No. 60/802,685, filed on May 23, 2006.

(51) Int. Cl.
*A61B 18/14* (2006.01)
(52) U.S. Cl. .............. 606/41; 606/28; 607/117
(58) Field of Classification Search .......... 606/28, 606/41
See application file for complete search history.

(56) References Cited

U.S. PATENT DOCUMENTS

| | | | | |
|---|---|---|---|---|
| 4,907,589 A * | 3/1990 | Cosman | | 606/34 |
| 5,122,137 A * | 6/1992 | Lennox | | 606/40 |
| 5,348,554 A * | 9/1994 | Imran et al. | | 606/41 |
| 5,433,739 A * | 7/1995 | Sluijter et al. | | 607/99 |
| 5,545,161 A * | 8/1996 | Imran | | 606/41 |
| 5,599,346 A * | 2/1997 | Edwards et al. | | 606/41 |
| 5,697,927 A * | 12/1997 | Imran et al. | | 606/41 |
| 5,935,123 A * | 8/1999 | Edwards et al. | | 606/41 |
| 5,980,504 A * | 11/1999 | Sharkey et al. | | 604/510 |
| 5,997,532 A * | 12/1999 | McLaughlin et al. | | 606/41 |
| 6,095,149 A * | 8/2000 | Sharkey et al. | | 128/898 |
| 6,096,035 A * | 8/2000 | Sodhi et al. | | 606/41 |
| 6,146,380 A * | 11/2000 | Racz et al. | | 606/41 |
| 6,246,912 B1 | 6/2001 | Sluijter et al. | | |
| 6,253,086 B1 * | 6/2001 | Parantainen et al. | | 455/446 |
| 6,479,605 B1 * | 11/2002 | Franchina | | 526/245 |
| 6,604,003 B2 * | 8/2003 | Fredricks et al. | | 607/99 |
| 6,726,685 B2 * | 4/2004 | To et al. | | 606/50 |
| 6,878,155 B2 * | 4/2005 | Sharkey et al. | | 607/96 |
| 7,267,683 B2 * | 9/2007 | Sharkey et al. | | 607/96 |
| 2001/0025177 A1 * | 9/2001 | Woloszko et al. | | 606/41 |
| 2001/0032001 A1 * | 10/2001 | Ricart et al. | | 607/99 |
| 2002/0147444 A1 * | 10/2002 | Shah et al. | | 606/28 |
| 2003/0060842 A1 * | 3/2003 | Chin et al. | | 606/170 |
| 2004/0210290 A1 | 10/2004 | Omar-Pasha | | |
| 2005/0004634 A1 * | 1/2005 | Ricart et al. | | 607/99 |
| 2005/0273093 A1 * | 12/2005 | Patel et al. | | 606/41 |
| 2006/0178666 A1 * | 8/2006 | Cosman et al. | | 606/41 |

* cited by examiner

*Primary Examiner* — Roy Gibson
*Assistant Examiner* — Kaitlyn Smith
(74) *Attorney, Agent, or Firm* — Fish & Associates, PC

(57) ABSTRACT

A catheter apparatus includes a hollow needle having an open, sharpened tip at its distal end. A cannula is telescopically disposed within the needle. The cannula has a closed, blunt tip at its distal end, a hollow lumen, and an open proximal end. The cannula is made of a flexible metal material and has an insulating material covering except at its distal portion defining the distal end. A metallic wire capable of transmitting radio frequency (RF) energy is telescopically disposed within the cannula. The cannula lumen has a seating surface for accommodating the distal end of the wire. The cannula distal end is capable of extending beyond the needle so that the blunt tip may be seated in a critical treatment region in a patient's spinal canal without damaging any nerves. A method of treating a patient's pain includes a step of inserting the catheter apparatus into a critical treatment region in the spinal canal of the patient. Once the needle is located near the treatment region, the cannula is advanced until the blunt tip extends beyond the needle's distal end. RF energy is then transmitted through the wire, the cannula's blunt tip, and to the treatment region.

9 Claims, 2 Drawing Sheets

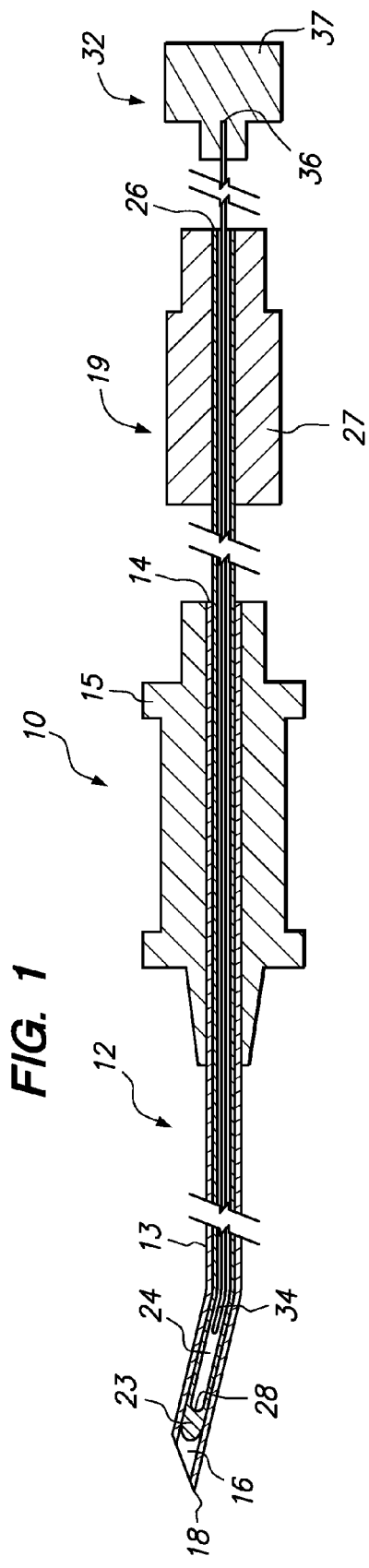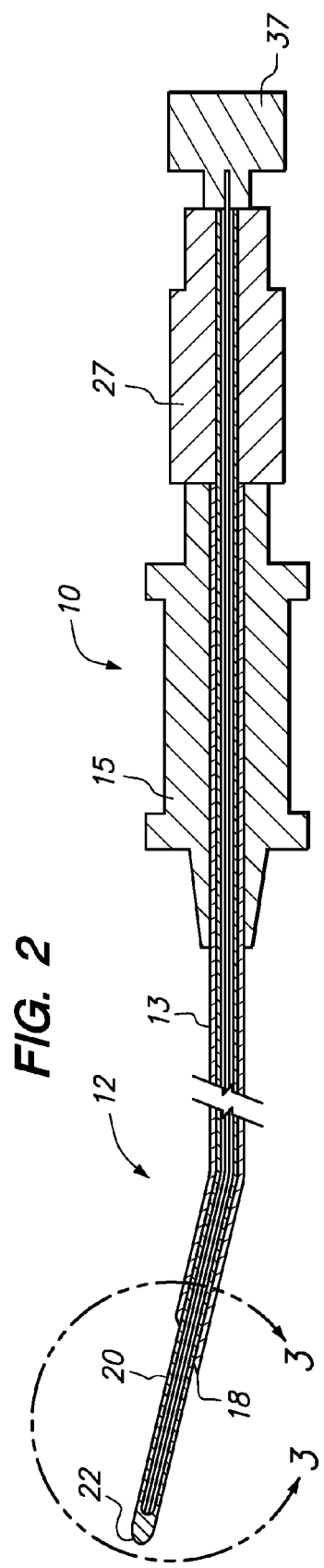

HIGH FREQUENCY EPIDURAL NEUROMODULATION CATHETER FOR EFFECTUATING RF TREATMENT IN SPINAL CANAL AND METHOD OF USING SAME

CROSS-REFERENCE TO RELATED APPLICATIONS

This application claims the benefit of U.S. Provisional Application No. 60/802,685, filed on May 23, 2006, the teachings of which are expressly incorporated by reference.

STATEMENT RE: FEDERALLY SPONSORED RESEARCH/DEVELOPMENT

Not Applicable

BACKGROUND OF THE INVENTION

1. Field of the Invention

The present invention relates generally to medical devices, and more particularly to an improved catheter for providing radio frequency (RF) treatment to a prescribed region within the spinal canal of a patient. Further in accordance with the present invention, there is provided a method for utilizing such a catheter.

2. Background Art

Radiofrequency (RF) treatment of pain has a long history in the field of pain management, and has been extensively utilized for the treatment of spine pain due to facet joint origin, in particular. Typically, a hollow cannula whose tip is sharp may be inserted percutaneously and positioned under fluoroscopic monitoring over the medial branch nerves that supply the involved facet joints. A probe whose tip emits radiofrequency energy is inserted into the hollow cannula, and causes tissue to heat around the un-insulated cannula tip, resulting in a thermal lesion to the medial branch nerves. With the nerves to the facets joints deactivated, the joints are no longer painful.

Unfortunately, thermal lesions to spinal nerve roots or other painful peripheral nerves often result in a worsening of the pain due to a thermal neuritis. Recently, a non-thermal mode of lesioning using a "pulsed" RF energy has become available with remarkably good results for pain relief. This technique does not produce neuritis, and has allowed for successful RF treatment of painful peripheral nerves. In addition, the technique has been applied to spinal nerve root pain sources, including the Dorsal Root Ganglion (DRG). Pulsed RF lesioning of the DRG has been extensively utilized using a transforaminal approach with generally good results. However, spinal stenosis, post-operative scarring, or other conditions may make the DRG inaccessible via a transforaminal approach; in such a setting, there is no currently available device or technique for performing RF treatment.

Spinal Cord Stimulators are also frequently utilized to target the dorsal root ganglion via the epidural space for treatment of pain stemming from spinal nerve root source. This may be due to conditions such as post herpetic neuralgia, radiculitis from disc disease or foraminal stenosis, post laminectomy syndrome or other neuropathies. The epidural space is accessed through a large bore epidural needle (17 G or 16 G) and then the SCS catheter is inserted into the epidural space and advanced to the target DRG under fluoroscopic guidance. The SCS catheter, once positioned, delivers a current of electrical energy that produces a paresthesia that effectively masks the pain stimulus. If the pain responds to the electrical stimulation, the SCS lead and an electrical generator is permanently implanted within the patient. This procedure with the SCS lead and generator has costs in excess of $20,000, and many patients do not desire a foreign body to be surgically implanted. Furthermore, SCS only serves to disrupt the pain signals by creating a competing parasthesia signal, which can be unpleasant or ineffective for some patients, rather than creating a lesion on the nerves which actually blocks the pain signals from being transmitted. Accordingly, RF lesioning can be more effective for pain management than SCS treatment without having to permanently implant medical devices within a patient.

The pain relief obtained with RF lesioning is similar between the non-thermal pulsed lesioning mode as it is with the standard high temperature lesioning. This suggests that the thermal aspects of the lesion are not the critical elements for obtaining long-term pain relief. The simple application of the radiofrequency electric field appears to be the primary factor. There is emerging substantial body of evidence that the radiofrequency electric field energy when applied to the DRG has neurophysiologic and neurobiological effects at the dorsal horn within the spinal cord. Indeed, the true origin of pain relief from RF treatment may be due to cellular effects on the dorsal horn neurons of the spinal cord, rather than a peripheral thermal lesion of the spinal/peripheral nerve. This evidence suggest that perhaps the dorsal column itself may be a potential target for therapy using RF electric field energy and obtaining sustained pain relief. In this regard, the epidural RF device may also be easily positioned over the dorsal column of the spinal cord, similar to the standard SCS lead placement, and it would be possible to deliver RF energy directly to the dorsal horn. In summary, the epidural radiofrequency catheter is a new device that has current applications for the treatment of spine and nerve pain, and has potential other therapeutic application by way of providing radiofrequency electric field energy to structures within the spinal canal.

Epidural anesthesia is also well known in the medical arts; that is, injecting pain medication through a catheter directly into the epidural space of a patient's spinal canal. However, the analgesic effect of epidural anesthesia is only of a temporary nature. Furthermore, it is impractical and inconvenient to provide repeated epidural injections to a patient for use as a long-term pain management solution.

Accordingly there is a need in the art for a catheter capable of providing RF lesioning treatment directly to critical areas without substantially risking permanently damaging the nerves located in the treatment region. There is also a need in the art for a method of relieving a patient's pain by administering RF energy directly to the patient's spinal nerves. In this regard, a device that can access the DRG via the epidural space, similarly to the SCS lead, and can deliver radiofrequency energy would provide a means of performing radiofrequency treatment to the DRG that is not possible with current technology. This would be an effective, less expensive alternative treatment for spinal nerve pain in patients who are not candidates for, or do not desire, implantable SCS catheter placement.

BRIEF SUMMARY OF THE INVENTION

In accordance with one aspect of the present invention, a catheter apparatus includes a needle having an open proximal end, a hollow lumen, and a sharpened tip at an open distal end. A closed-end cannula is telescopically disposed within the needle lumen. The cannula has an exterior blunt tip at its distal end, a hollow lumen, and an open proximal end. Additionally, the cannula is made of a flexible metal and has an insulating material covering that substantially encapsulates the length of the cannula, except for a distal portion which defines the distal end of the cannula and hence the closed, blunt tip thereof. A metallic wire element capable of transmitting radio frequency (RF) energy and having proximal and distal ends is telescopically advanced within the cannula lumen. The distal end of the cannula lumen (i.e., the end of the lumen adjacent the distal end or tip of the cannula) is defined by an interior seating surface of the cannula which is configured to be complementary to the distal end of the wire, thus providing a surface against which the distal end of the wire may be operatively seated. The length of the cannula is greater than the length of the needle. As such, the cannula distal end is capable of being extended beyond the needle distal end so that the blunt tip may be seated or otherwise positioned in the desired treatment region or site within the spinal canal of a patient. At the same time, the cannula proximal end extends beyond the needle proximal end so that the cannula may be manipulated by the user, typically under the guidance or assistance of X-rays. Similarly, the wire element is of a sufficient length so that the distal end of the wire element is capable of being abutted against and thus cooperatively engaged in energy transmitting fashion to the seating surface defined by the cannula. At the same time the proximal end of the wire element extends beyond the cannula proximal end, thus allowing the wire element to be operatively connected to a suitable RF generating device.

In accordance with another aspect of the invention, a method of treating a patient's pain includes the initial step of inserting a catheter apparatus into a critical treatment region of the patient which, in accordance with the present invention, is contemplated to reside within the spinal canal of the patient. The catheter apparatus includes a needle having an open proximal end, a hollow lumen, and a sharpened tip at an open distal end. A closed-end cannula is telescopically advanced through the lumen of the needle. As indicated above, the cannula has an exterior blunt tip at its distal end, a hollow lumen, and an open proximal end. The cannula is advanced through the lumen of the needle until the blunt tip thereof extends beyond the distal end of the needle and is seated or positioned at the desired treatment region within the spinal canal of the patient. Imaging techniques, including X-ray imaging, may be used in order to visually monitor the proper placement or positioning of the blunt tip at the desired treatment site within the patient. A metallic wire element capable of transmitting RF energy is then inserted into the lumen of the cannula and advanced therein until such time as the distal end of the wire element abuts and thus is seated against a seating surface defined by the cannula and located at the distal end of the lumen thereof. The proximal end of the wire is then attached to an RF generating machine which transmits the RF energy through the wire, to the cannula's blunt tip, and ultimately to the treatment region.

The catheter apparatus of the present invention is envisioned as one capable of accessing the epidural space, similar to the SCS, and directed to the desired DRG using standard fluoroscopic monitoring technique. The cannula of the catheter apparatus is entirely shielded with non-conducting material, except the distal 10 mm active tip, which is blunt and curved. This is similar to the design of a standard radiofrequency cannula, but of much greater flexibility and length. Once positioned over the DRG by fluoroscopic guidance, the device may be attached to a standard radiofrequency generator, and 50 Hz sensory stimulating current may be applied. The sensory stimulation is utilized to make small adjustments in the cannula position, thereby obtaining precise physiologic localization of the cannula tip over the desired DRG. The cannula tip may be curved to allow steerage, and is blunt to reduce risk of entering the spinal thecal sac, or cause direct nerve damage to the DRG. The cannula is also constructed to accept a standard radiofrequency probe that typically have a built in thermistor to measure temperature at the tip in real time, and to deliver pulsed radiofrequency energy. The cannula is designed to allow radiofrequency energy to be applied directly to the DRG via the epidural route. This technique may be performed in instances where the transforaminal approach is not feasible, or may even prove to become the preferred approach depending on the clinical results.

Other objects and advantages of the invention will be apparent to those skilled in the art from a review of the following detailed description, taken in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a partially exploded, cross-sectional view of a catheter apparatus constructed in accordance with the present invention;

FIG. 2 is a cross-sectional view of the catheter apparatus shown in FIG. 1 in a fully assembled state;

DETAILED DESCRIPTION OF THE INVENTION

Figure 3:
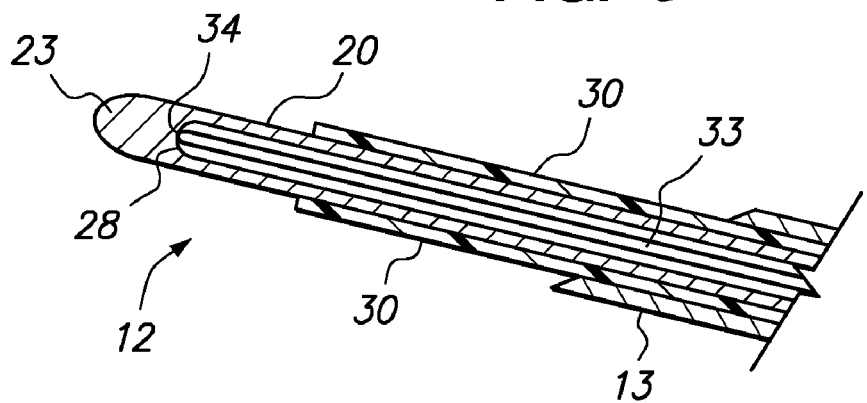
FIG. 3 is an enlargement of the encircled region 3-3 shown in FIG. 2.

Referring now to the drawings, which are illustrative of one embodiment of the present invention only and are not for purposes of limiting the same, FIG. 1 shows a partially assembled catheter apparatus 10 constructed in accordance with the present invention. As shown in FIGS. 1 and 2, the catheter apparatus 10 includes a needle assembly 12 having an elongate needle 13. The needle 13 of the needle assembly 12 has an open proximal end 14 which is defined within one end of an enlarged needle hub 15 of the needle assembly 12, the needle 13 being partially disposed with the needle hub 15 in the manner shown in FIGS. 1 and 2. The needle hub 15 is configured to be easily graspable to allow for the insertion of the needle 13 of the needle assembly 12 to a desired treatment site, as will be described in more detail below. The needle 13 of the needle assembly 12 further includes a hollow lumen 16 and an open distal end 18. The distal end 18 of the needle 13 is itself defined by a sharpened tip for penetrating a patient's tissue. As indicated above, the needle assembly 12 may be manipulated (i.e., the distal end 18 of the needle 13 advanced through the patient's tissue to a desired treatment site with the spinal canal) by grasping the needle hub 15 thereof.

The catheter apparatus 10 of the present invention further comprises a cannula assembly 19 which is cooperatively engageable to the needle assembly 12 in the manner shown in FIGS. 1 and 2. The cannula assembly 19 comprises an elongate, flexible cannula 20 which is telescopically disposed within and selectively advanceable through the lumen 16 of the needle 13 of the needle assembly 12. The cannula 20 includes a closed distal end 22 which is itself defined by a blunt tip having a generally semi-spherical outer surface. In addition to the distal end 22, the cannula 20 further defines a hollow lumen 24 and an open proximal end 26. The proximal end 26 of the cannula 20 is defined within an enlarged cannula hub 27 of the cannula assembly 19, the cannula 20 being partially disposed within the cannula hub 27 in the manner also shown in FIGS. 1 and 2. As is best seen in FIG. 3, the cannula 20 includes a distal portion 23 which extends to and defines the distal end 22 thereof. The distal portion 23 of the cannula 20 further defines an interior seating surface 28 which has a generally concave configuration. The use of the seating surface 28 will be discussed in more detail below.

In the catheter apparatus 10 of the present invention, it is contemplated that the cannula 20 of the cannula assembly 19 will be constructed from a flexible metal material that is capable of transmitting radio frequency (RF) energy. Further, as seen in FIGS. 2 and 3, it is contemplated that a substantial portion of the length of the cannula 20 will be covered or encapsulated by a layer 30 of a suitable insulating material. As seen in FIG. 3, the layer 30 is sized relative to the cannula 20 such that the distal end of the layer 30 terminates inward of the distal portion 23 (and hence the distal end 22) of the cannula 20 by a prescribed distance. Thus, since the distal portion 23 of the cannula 20 is not covered by the layer 30 of the insulating material, RF energy is capable of being freely transmitted from the distal portion 23 of the cannula 20, including the distal end 22 thereof. It is contemplated that the outer diameter of the cannula 20 of the cannula assembly 19 and the inner diameter of the needle 13 (i.e., the diameter of the lumen 16) will be sized relative to each other within a prescribed tolerance range which permits the slidable movement of the cannula 20 through the lumen 16, yet presents a close enough fit to substantially inhibit fluid leakage therebetween.

The catheter apparatus of the present invention further comprises an RF transmission assembly 32 which is itself cooperatively engageable to the cannula assembly 19. The RF transmission assembly 32 comprises an elongate, metallic wire element 33 which is capable of conveying or transmitting RF energy received from an RF generating source (not shown). The wire element 33 defines a distal end 34 and an opposed proximal end 36 which resides within an adapter hub 37 of the RF transmission assembly 32. The adapter hub 37 is itself configured to be operatively coupled to the RF generating source in a manner which effectively facilitates the transmission of RF energy from the RF generating source into the wire element 33. In the catheter apparatus 10, the wire element 33 is advanced within the lumen 24 of the cannula 20 until such time as the distal end 34 of the wire element 33 is abutted or firmly seated against the seating surface 28 defined by the cannula 20, as shown in FIG. 3. In this regard, it is contemplated that the distal end 34 of the wire element 33 and the seating surface 28 of the cannula 20 may be formed to have complimentary configurations which facilitate the firm seating or engagement therebetween when the wire element 33 is fully advanced through the lumen 24 of the cannula 20. As will be recognized by those of ordinary skill in the art, the abutment of the distal end 34 of the wire element 33 against the seating surface 28 of the cannula 20 allows RF energy transmitted through the wire element 33 to be effectively transmitted to and from the distal end 22 of the cannula 20 upon the activation of the RF generating source.

As shown in FIG. 2, the length of the cannula 20 exceeds the length of the needle 13 such that when the cannula assembly 19 is operatively coupled to the needle assembly 12 (i.e., the cannula hub 27 engages the needle hub 15), the distal portion 23 of the cannula 20 will protrude well beyond the distal end 18 of the needle 13. Along these lines, it is contemplated that the RF transmission assembly 32 and the cannula assembly 19 may be sized relative to each other such that the engagement of the adapter hub 37 to the cannula hub 27 in the manner shown in FIG. 2 effectively facilitates the abutment or engagement of the distal end 34 of the wire element 33 to the seating surface 28 of the cannula 20. Since the distal portion 23 of the cannula 20 protrudes from the distal end 18 of the needle 13 when the cannula assembly 19 is cooperatively engaged to the needle assembly 12 in the above-described manner, the blunt distal end 22 of the cannula 20 is capable of being positioned at a desired treatment region within the spinal canal of a patient. Such positioning or placement may be effectuated without causing sheering damage to the treatment region due to the absence of any sharpened point or tip on the distal portion 23 of the cannula 20. As indicated above, the positioning of the distal end 22 of the cannula 20 at the appropriate treatment site within the spinal canal of the patient is facilitated by the selective manipulation of the cannula hub 27 of the cannula assembly 19 by the user, typically under the guidance or assistance of X-rays.

Figure 4:
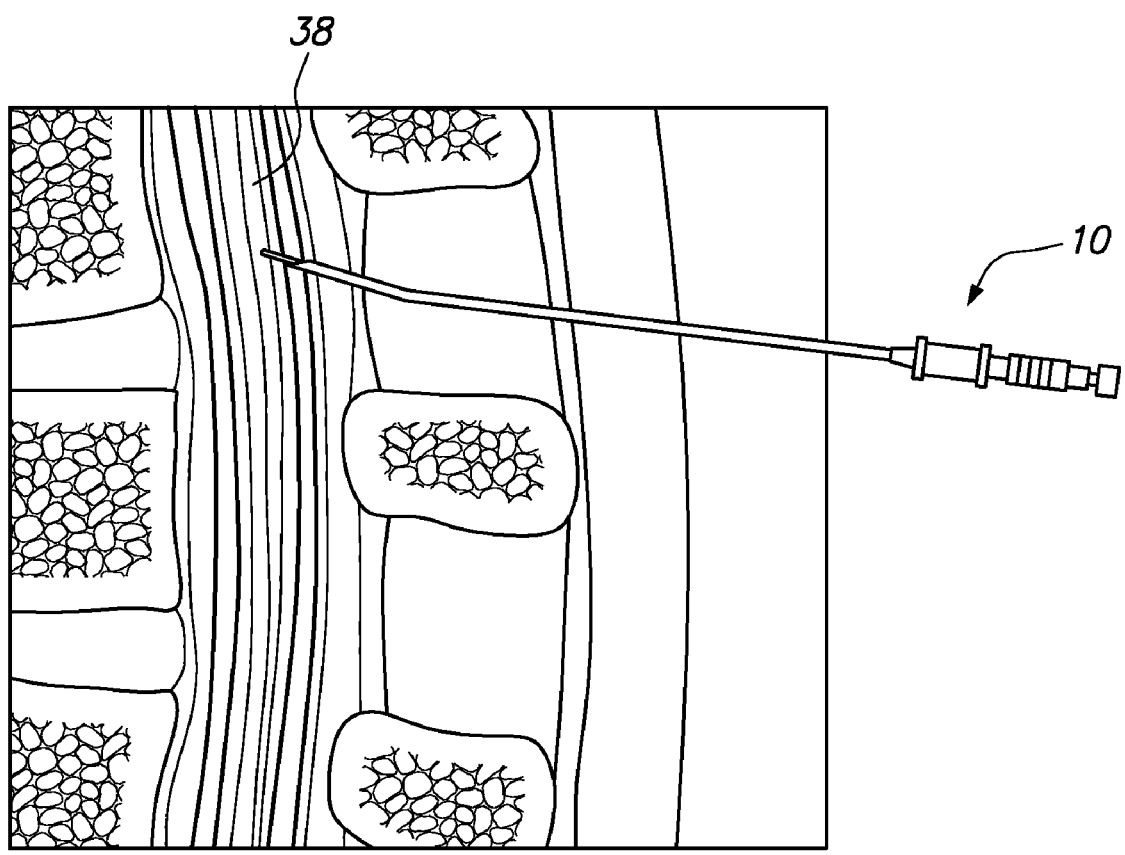
FIG. 4 is a side elevational view illustrating an exemplary positioning of the catheter apparatus of the present invention within a patient's spinal canal.

An exemplary technique which may be used to facilitate the use of the catheter apparatus 10 of the present invention for treating a patient's pain comprises the initial step of partially advancing the cannula 20 of the cannula assembly 19 into the lumen 24 of the needle 13 of the needle assembly 12. More particularly, the advancement of the cannula 20 within the lumen 24 is limited such that the distal end 22 of the cannula 20 does not protrude beyond the distal end 18 of the needle 13. Since the distal end 22 does not protrude beyond the sharpened distal end 18, the user of the catheter apparatus 10 is able to use the sharpened distal end 18 of the needle 13 to pierce or penetrate the patient's tissue adjacent the desire treatment site. Subsequent to the partial insertion of the needle 13 into the spinal canal 38 of the patient, the advancement of the cannula 20 through the lumen 24 of the needle 13 is continued to facilitate the extension of protrusion of the distal portion 23 of the cannula 20 from the distal end 18 of the needle 13 in the manner shown in FIGS. 2, 3 and 4. Again, imaging techniques, including x-ray imaging, may be used to visually assist the user in properly placing or positioning the distal end 22 of the catheter 20 at the desired treatment site within the patient's spinal canal 38. Once the distal end 22 of the cannula 20 has been properly positioned at the desired treatment region within the spinal canal 38 of the patient in the manner shown in FIG. 4, it is contemplated that the needle assembly 12 may be removed from the cannula assembly 19, thus leaving only the cannula 20 within the body of the patient. In this regard, there is known in the medical arts needle assemblies which are specifically adapted to be split to allow for the removal thereof from a cannula assembly after the needle assembly has been used to penetrate or pierce the patient's tissue.

After the distal end 22 of the cannula 20 has been properly positioned at the desired treatment site within the patient's spinal canal 38, the RF transmission assembly 32 is cooperatively engaged to the cannula assembly 19 in the above-described manner, thus effectuating the abutment of the distal end 34 of the wire element 33 against the seating surface 28 defined by the distal portion 23 of the cannula 20. Subsequent to such abutment or engagement and the operative coupling of the adapter hub 37 to the RF generating source, the activation of such RF generating source/machine facilitates the transmission of RF energy along the wire element 33, through the distal portion 23 of the cannula 20, and to the distal end 22 thereof and hence into the treatment region within the spinal canal 38 of the patient. Upon the completion of the treatment, the catheter 20, which may still include the wire element 33 operatively positioned therein, is simply withdrawn from within the spinal canal 38 of the patient.

Advantageously, because the distal end 22 of the cannula 20 has a closed, blunt configuration, critical treatment areas within the spinal canal 38 of the patient may be reached with substantially reduced risk of permanently damaging the nerves to be treated as could occur by any attempted placement of the sharpened tip of a needle near such nerves. In this regard, the sharpened distal end 18 of the needle 13 need not be placed in close proximity to the treatment region within the spinal canal 38 of the patient due to the capability of advancing the distal portion 23 of the cannula 20 substantially beyond the distal end 18 through the use of the catheter apparatus 10 of the present invention. Thus, due to its structural and functional attributes, the catheter apparatus 10 of the present invention is capable of being used in critical treatment areas within the spinal canal 38 of a patient that would otherwise not be amenable to RF energy treatment.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. For example, though the catheter apparatus 10 of the present invention has been described above as being optimal for use in effectuating treatment within the spinal canal of a patient, those of ordinary skill in the art will recognize that the structural and functional attributes of the catheter apparatus 10 also lend themselves to the use thereof in relation to alternative treatment sites outside of the spinal canal.

What is claimed is:

1. A catheter delivery device to transmit radiofrequency energy to a spinal canal, comprising:
    a needle having an open proximal end and an open distal end, and a lumen that extends from the open proximal end to the open distal end;
    a catheter having a blunt, metallic tip on a distal end of the catheter that transmits a radio frequency energy to the treatment site, wherein the catheter is telescopically disposed within the needle lumen to allow the tip to be maneuverably positioned within the spinal canal;
    a catheter hub coupled to a proximal end of the catheter
    a metallic wire element telescopically disposed within a lumen of the catheter; and
    an adapter hub coupled to a proximal end of the wire element, wherein the adapter hub is cooperatively engageable to the catheter hub to form a single shaft,
    wherein a proximal end of the adapter hub is configured couple to a radio frequency generating device, and wherein the adapter hub and the catheter hub are sized and dimensioned relative to one another such that engagement of the adapter hub to the catheter hub allows a distal end of the wire element to touch a seating surface of the tip such that the wire element delivers a radio frequency energy from the radio frequency generating device to the tip.

2. The device of claim 1, wherein a length of the catheter is longer than a length of the needle.

3. The device of claim 1, wherein the catheter is flexible.

4. The device of claim 1, further comprising a layer of insulating material coupled to a portion of the catheter, wherein the insulating material prevents a radio frequency energy from transmitting.

5. The device of claim 4, wherein the insulating material encapsulates all but the distal end of the catheter.

6. The device of claim 5, wherein the insulating material terminates 10 mm from the distal end of the catheter.

7. The device of claim 1, wherein a portion of the catheter is not straight to improve steerage of the catheter.

8. The device of claim 1, wherein the distal end of the needle is sharpened to penetrate an outer layer of the treatment site.

9. The device of claim 1, wherein the distal end of the wire element and the seating surface of the tip are formed to have complementary configurations to facilitate the engagement between the distal end of the wire element and the seating surface of the tip.

* * * * *